United States Patent [19]

King

[11] Patent Number: 5,317,155
[45] Date of Patent: May 31, 1994

[54] CORONA DISCHARGE APPARATUS

[75] Inventor: Ray J. King, Carolina Beach, N.C.

[73] Assignee: The Electrogesic Corporation, New York, N.Y.

[21] Appl. No.: 997,907

[22] Filed: Dec. 29, 1992

[51] Int. Cl.$^5$ ............................................. H01T 19/04
[52] U.S. Cl. ..................................... 250/324; 361/235
[58] Field of Search ......................... 250/324; 361/235

[56] References Cited

U.S. PATENT DOCUMENTS

| | | | |
|---|---|---|---|
| 3,563,246 | 2/1971 | Puharich et al. | 128/422 |
| 3,617,684 | 11/1971 | Di Mino | 219/121 R |
| 3,699,388 | 10/1972 | Ukai | 250/324 |
| 3,736,492 | 5/1973 | Rosenthal et al. | 321/45 R |
| 3,736,493 | 5/1973 | Rosenthal et al. | 250/324 |
| 4,166,690 | 9/1979 | Bacon et al. | 355/3 C H |
| 4,572,194 | 2/1986 | Head | 128/419 R |
| 4,667,677 | 5/1987 | Di Mino | 128/419 R |
| 4,705,931 | 11/1987 | Di Mino | 219/68 |
| 4,713,220 | 12/1987 | Huynh et al. | 422/186.16 |
| 4,714,911 | 12/1987 | Di Mino | 338/195 |
| 5,109,847 | 5/1992 | Liss et al. | 128/421 |
| 5,131,904 | 7/1992 | Markoll | 600/14 |

FOREIGN PATENT DOCUMENTS

| | | |
|---|---|---|
| 818045 | 10/1966 | Canada . |
| 2907013 | 8/1979 | Fed. Rep. of Germany . |
| 2336145 | 12/1975 | France . |
| 266086 | 2/1969 | U.S.S.R. . |
| 1156153 | 6/1969 | United Kingdom . |

OTHER PUBLICATIONS

"The Latest Technology in ElectroAcupuncture Russian MRT (Microwave Resonance Therapy)," Tesla Scalar Frequencies Rapid Elimination of Pain, Council of Ministers Ukr. SSR (Prob. 1989).

Crawford et al., "Pulsed Radio Frequency Therapy of Experimentally Induced Arthritis in Ponies," Can J Vet Res 1991; vol. 55: pp. 76-85.

Brown, T., "The Lakhovsky Multiple Wave Oscillator Handbook," Borderland Sciences Research Foundation, Garberville, CA (1988) pp. 20-34, 43-48, 68.

Primary Examiner—Bruce C. Anderson
Attorney, Agent, or Firm—Mason, Fenwick & Lawrence

[57] ABSTRACT

A power amplifier for use in medical and veterinary testing and therapy. A tunable pulse-width-modulated signal generator is connected to a gating element to provide a digital waveform suitable for comprehensive control of the waveform shape and average output power provided by the apparatus. The digital waveform controls a power driver. Through use of a high-Q resonant circuit including a capacitor and a primary winding of a coil assembly, a voltage of about 150–400 volts is increased to about 10 kilovolts at the primary winding. The coil assembly has a secondary:primary turns ratio of 10:1, resulting in a signal of about 100 kilovolts at the output of the secondary winding. This arrangement produces a corona discharge at a discharge pin connected to the secondary winding. A manual tuning embodiment and a self-tuning embodiment are disclosed.

6 Claims, 7 Drawing Sheets

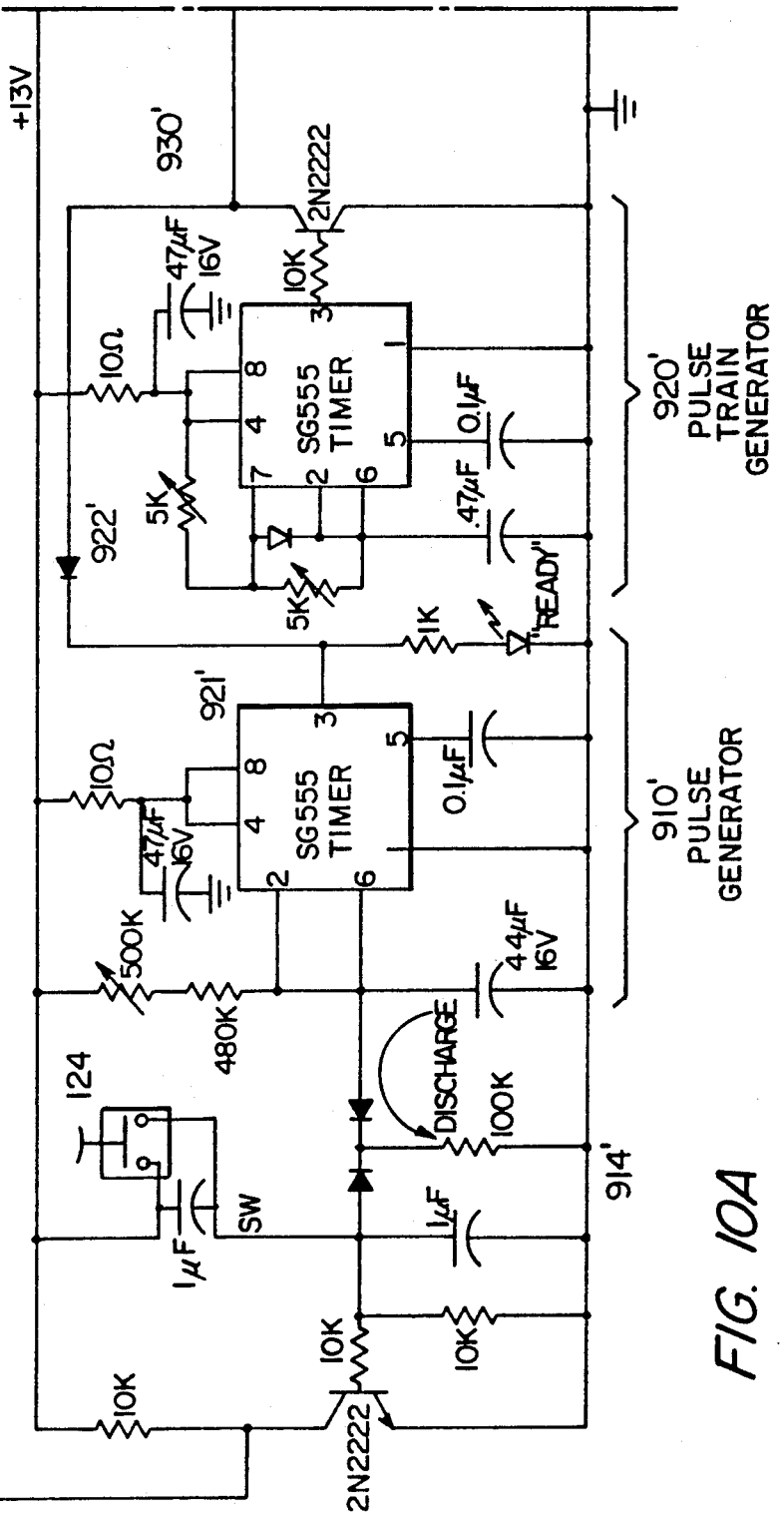

CORONA DISCHARGE APPARATUS

BACKGROUND OF THE INVENTION

1. Field of the Invention

The present invention relates to corona discharge apparatus including electric power amplifiers, especially suitable for use in medical and veterinary testing and therapy.

2. Related Art

A corona discharge beam is a discharge of electricity produced on the surface of and adjacent to a conductor when the voltage gradient produced by a high voltage exceeds a certain critical value due to ionization of the surrounding air by the high voltage. Corona discharge beams for use in thermotherapy treatment in general and for use in trimming thick film resistors are known in the art.

As a background, U.S. Pat. No. 4,667,677 (Di Mino) discloses a thermotherapy technique in which a beam is used to apply heat to a patient's skin to treat arthritis and other medical conditions. A corona discharge beam is derived from a low radio-frequency power source in which a low radio-frequency carrier in the range of 200 to 300 kHz is overmodulated by a sonic frequency signal in the 3000 to 5000 Hz range to produce a continuous energy waveform. The resulting bursts of radio-frequency energy have a repetition rate at the sonic frequency and a peak amplitude sufficient to cause a corona discharge in the energy range of 5 to 15 watts. The energy from this discharge is applied in 20 second and 30 to 40 second applications to generate heat in a patient.

In the field of trimming thick film resistors with corona discharge, U.S. Pat. No. 4,714,911 (Di Mino) discloses a technique for enhancing the electrical characteristics of thick film resistors to bring them to their target values. A generating unit in which a low radio-frequency carrier is overmodulated by a sonic signal to produce bursts of radio-frequency energy which is coupled to an UP probe by a step-up transformer and to a DOWN probe by a step-down transformer. By raising the value of the resistor above the desired target value with the UP probe and then decreasing its value with the DOWN probe the target value of the resistor is attained.

U.S. Pat. No. 5,131,904 (Markoll) discloses a method of treating arthritis by placing the affected body part in the field of an annular coil driven by a rectangular waveform.

These references, and all documents cited in this specification, are incorporated herein by reference.

The use of corona discharge to treat mammalians has been known since at least the beginning of the twentieth century, as evidenced by the work of Nicola Tesla as told by Margaret Cheney in *TESLA: Man Out of Time* (Dell, 1981). The use of sonic frequencies to produce the energy wave to create a corona discharge have also been reported. It is clear from these references that the therapeutic use of corona discharge in general is recognized.

Unfortunately, known corona discharge beam devices and resistor trimming devices have shortcomings which limit their usefulness. There is a lack of appreciation of the importance of the waveform that generates the energy to produce to the corona discharge and of the nature of the corona discharge itself. Furthermore, the known applications of corona discharge emphasize the healing effect of the heat generated by the corona discharge and in only a limited way appreciate that the corona energy in and of itself, or the magnetic fields generated by the corona discharge apparatus itself, may have a therapeutic benefit. As a result, the known applications of corona discharge to mammalian therapeutic uses is limited by the lack of understanding of how to generate suitable corona discharges and/or magnetic fields that have beneficial uses, in addition to any thermotherapeutic utility.

Therefore, there is a need in the art to provide a corona discharge beam for therapy which make use of a specially produced waveform in generating energy to produce corona discharge. Moreover, there is a need to produce a therapeutic effect using the corona discharge energy itself or magnetic fields generated by the corona discharge apparatus, and not relying on incidental or additional thermotherapeutic attributes. Further, there is a need to provide a therapeutic device which provides reduced shock hazard to the patient. Of course, it is desirable to provide a therapeutic apparatus which is small, portable, flexible, conveniently adjustable, easy to use, and cost-effective.

It is to meet these and other needs that the present invention is directed.

SUMMARY OF THE INVENTION

The present invention solves the problems of known systems.

It is therefore a primary object of the present invention to provide a system for producing a corona discharge beam for treatment of medical conditions such as pain and inflammation, and for veterinary testing. The apparatus involves digital techniques for generation of waveforms resulting in specific corona discharge beams and magnetic fields. The apparatus includes a coil of special construction. Advantageously, the invention is safe and easy to use, flexible, conveniently adjustable, and is lightweight and portable due to preferred use of battery power as well as embodiments using AC power.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which:

FIG. 10 illustrates the arrangement of FIGS. 10A, 10B, and 10C. FIGS. 10A, 10B, and 10C (which may also be referred to herein as "FIG. 10", for brevity) collectively comprise a detailed circuit level diagram of the embodiment shown functionally in FIG. 1 and schematically in FIG. 9.

DETAILED DESCRIPTION OF THE PREFERRED EMBODIMENTS

Figure 1:
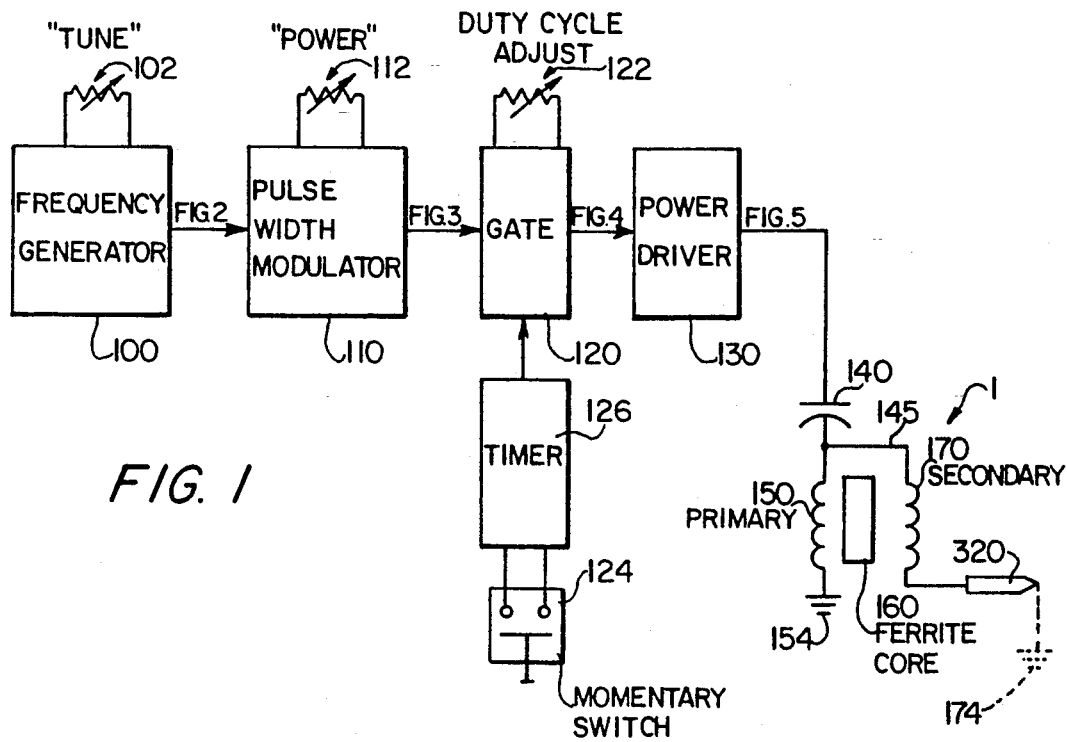
FIG. 1 is a high-level schematic functional block diagram showing the major functional blocks of a preferred corona discharge apparatus according to the present invention.

In describing preferred embodiments of the present invention illustrated in the drawings, specific terminology is employed for the sake of clarity. However, the invention is not intended to be limited to the specific terminology so selected, and it is to be understood that each specific element includes all technical equivalents which operate in a similar manner to accomplish a similar purpose.

The present invention provides an apparatus and method for generating specific signals so as to produce a corona discharge beam and magnetic fields for therapeutic treatment of medical conditions and veterinary testing. More particularly, the invention is useful in the treatment of pain and inflammation.

Briefly, a preferred embodiment of the present invention functions by employing a base frequency generator 100 which generates a 500 kHz square waveform. The generator 100 is connected to a pulse width modulator 110 for modulating the widths of the pulses of the base frequency wave. The modulator 110 is connected to a gate arrangement 120 which switches the modulated base frequency wave on and off repetitively in 660 Hz cycles in accordance with a duty cycle adjustment means and in accordance with a user's momentary trigger switch 124 and a timing circuit 126 responsive to the trigger switch. Next, the gated, modulated base frequency wave enters a power driver element 130. The power driver element 130 provides power to a high-Q coil assembly 1, which coil assembly in turn provides high voltage to a corona discharge pin 320.

The power driver 130 switches at 500 kHz and provides signals in the range of about 150 to 400 volts (depending on whether 120 VAC or 240 VAC input line power is used). Then, the 150–400 volt signal is stepped up to a range of 5–10 kilovolts, through use of a high-Q resonant circuit. To form the high-Q circuit, a capacitor is connected in series with a primary winding of a transformer in series-resonant fashion. The secondary winding in coil assembly 1 has a 10:1 turns ratio with the primary, so that voltages of about 100 kilovolt are produced on the output of the secondary coil.

Figure 10B:
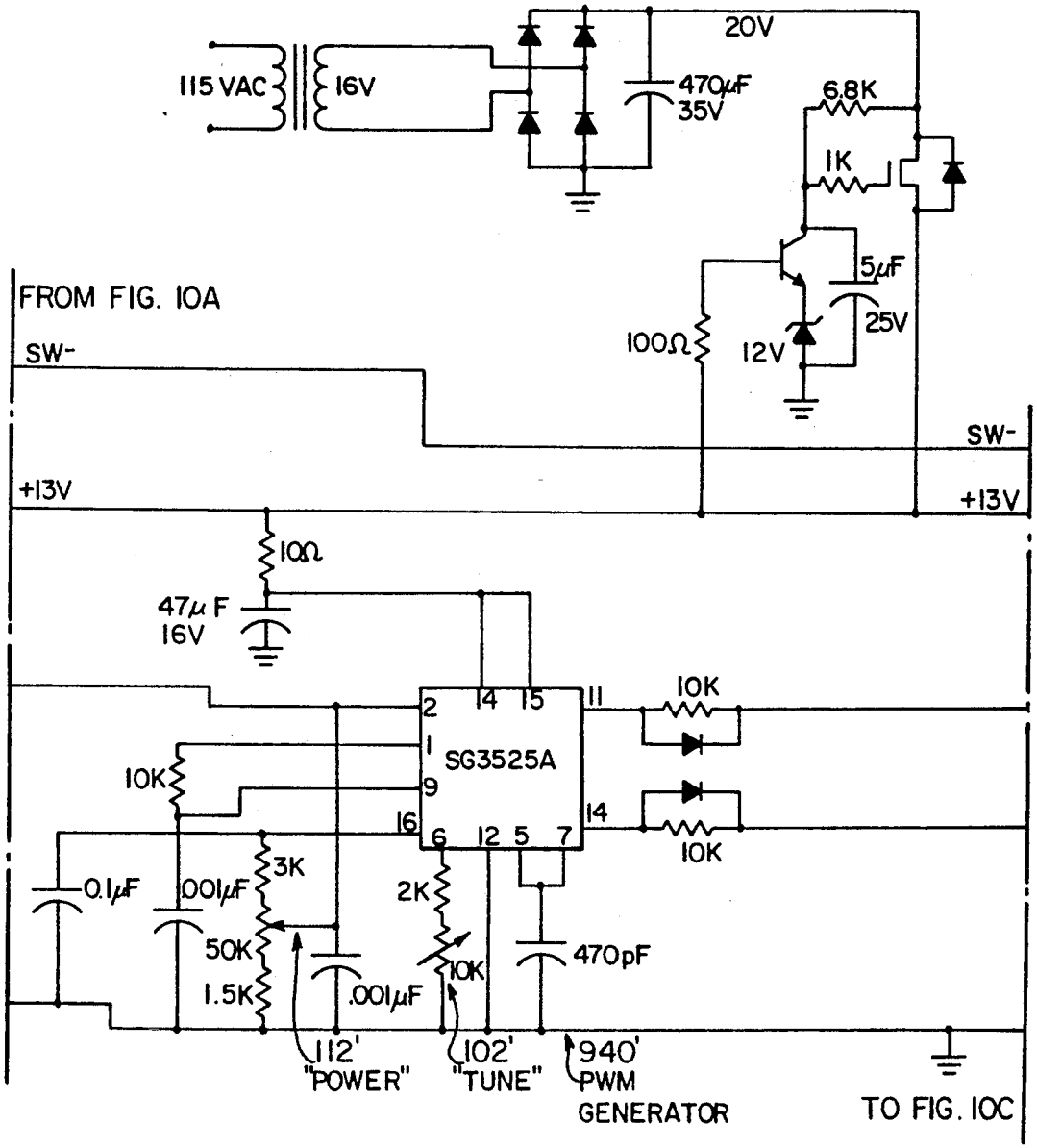
Figure 10C:
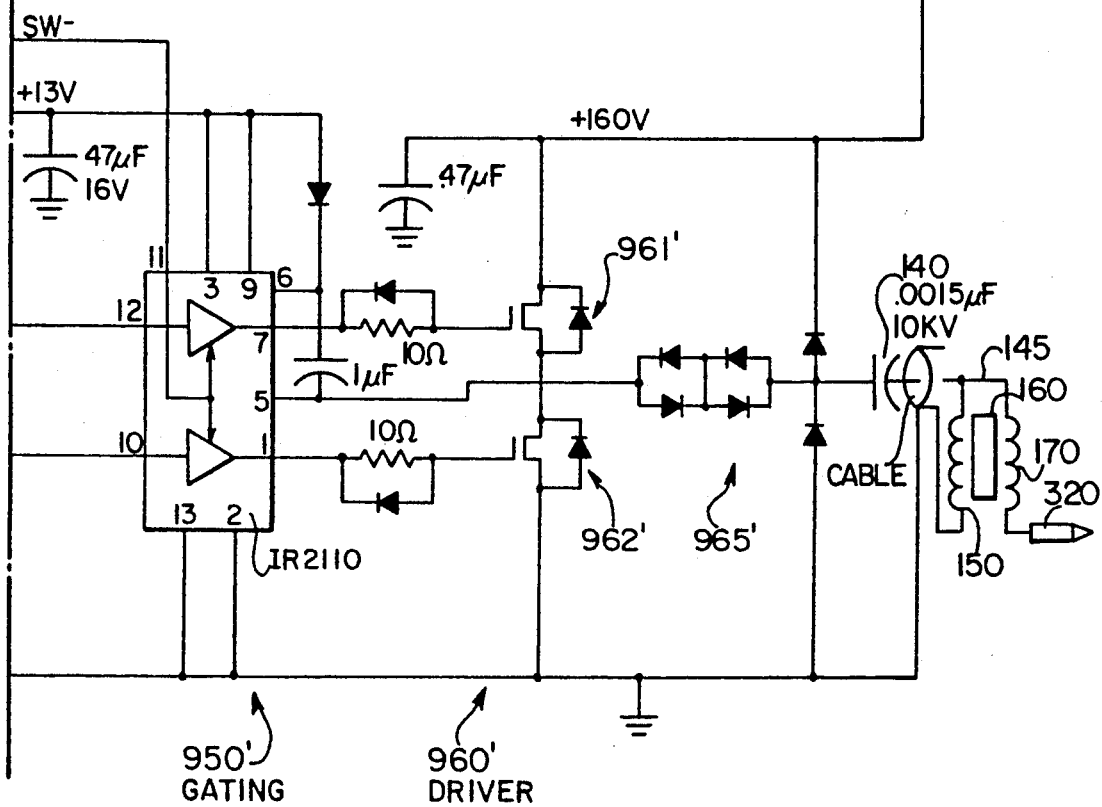
Figure 11:
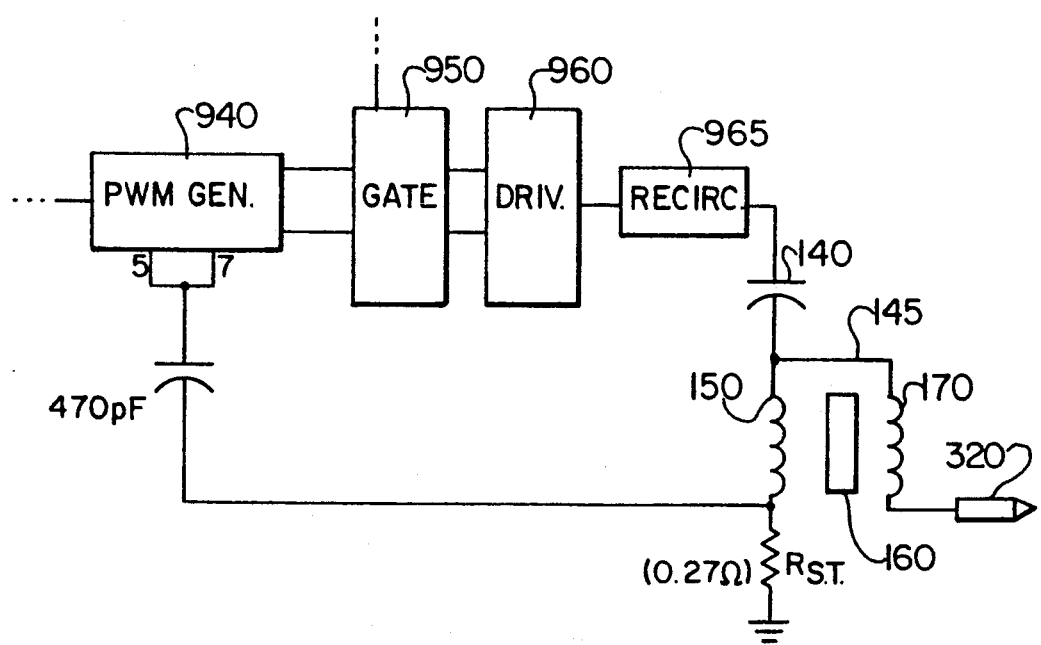
FIG. 11 illustrates a modification to the embodiment of FIGS. 10B and 10C which allows it to be a self-tuning device.

A preferred embodiment of the electronic power amplifier according to the present invention is shown and described in more detail with reference to FIGS. 1–10. Alterations to the first embodiment which are needed to form an alternative embodiment are shown in FIG. 11.

Referring now more specifically to FIGS. 1–5, a high-level functional description of the preferred embodiment of the invention is provided.

Figure 2:
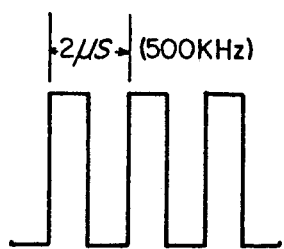
FIG. 2 illustrates the frequency-adjustable (normally 500 kHz) waveform output by base frequency generator 100.

The system includes a base frequency generator 100 which generates a square wave at approximately 500 kHz, as illustrated in FIG. 2. By a suitable adjustment means such as a variable resistor 102, the exact frequency may be adjusted to equal the resonant frequency of a high-Q resonant circuit associated with the output transformer of the coil assembly 1.

The base frequency generator is shown schematically, connected to a pulse width modulator (PWM) 110. The modulator 110 modulates the pulse widths of the 500 kHz wave generated by the base frequency generator 100, to adjust the power output of the entire apparatus. The width of pulses is adjustable by a suitable adjustment means such as a variable resistor 112. By increasing the width of the pulses, the long-term average output power is increased; conversely, by reducing the width Of the pulses, the long-term average output power is decreased.

Figure 3:
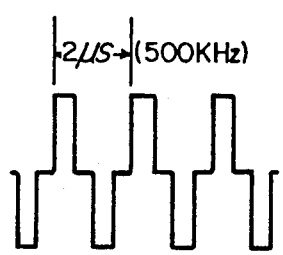
FIG. 3 illustrates the pulse-width modulated waveform output by pulse width modulator 110 in response to the waveform of FIG. 2.

The output of the pulse width modulator is shown in FIG. 3. As shown in FIG. 3, the PWM output comprises a series of pulses of alternating polarity, but the individual pulses are narrower than a pure 500 kHz bipolar square wave. Between successive alternating-polarity pulses are periods of zero volt output. The zero volt periods are shorter when the pulses are longer, and are longer when the Pulses are shorter. Regardless of the pulse widths, the overall waveform has a repetition frequency of 500 kHz.

As will be described in greater detail below, the base frequency generator 100 and pulse width modulator 110 may collectively be implemented as a SILICON GENERAL SG3525 PWM generator or equivalent, an off-the-shelf integrated circuit which is commonly used in switching power supplies. A potentiometer 102 for adjusting the generator's output frequency, as well as a potentiometer 112 for adjusting its output pulse width, are used directly with the SG3525.

The pulse width modulated 500 kHz wave enters a gate 120, which gates its input (reduces to zero amplitude) at a 660 Hz rate. The gate 120 effectively gates the 500 kHz pulse-width modulated signal of FIG. 3 against a gating wave (preferably 50% duty cycle) gating signal of 660 Hz. The envelope of the resultant gated waveform is shown in FIG. 4.

The frequency as well as the duty cycle of the gate's effective gating signal is adjustable by suitable adjustment means 122, as described in greater detail below. Within gating element 120, the pulse-width modulated signal is gated, either by the user removing his finger from the switch 124, by timeout of a timer circuit 126 responsive to the user switch, or by the "off" portion of the repetitive pulse train determined by duty cycle adjustment means 122.

This logic, wave shaping and gating is done at the logic power level (such as 12–13 volts), thus conserving power.

Figure 4:
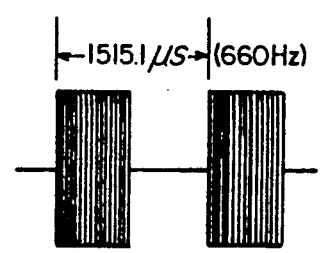
FIG. 4 illustrates the envelope of a waveform that is output by gate element 120, the envelope being "on" about half the time.
Figure 5:
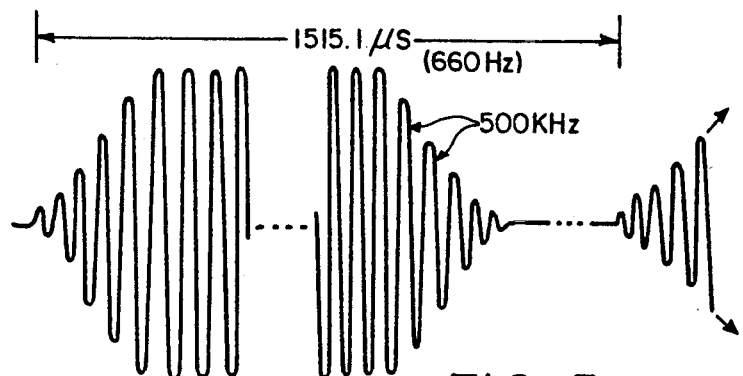
FIG. 5 illustrates the waveform output by power driver element 130 to the high-Q coil circuit.

The gated 500 kHz wave of FIG. 4 is fed into power driver 130. Power driver 130 preferably includes MOSFETs and fast-recovery diodes which are connected in a half bridge or bridge topology, so as to operate as power switches. The output of the power switches is a square wave which corresponds to the gated, pulse-width modulated signal output by the gate 120. The power switches switch at 500 kHz, and provide output in the range of 150 to 400 volts depending upon whether 120 VAC or 240 VAC is used to power the apparatus.

The 150-400 volt signal from power driver 130 is stepped up to a range of 5 to 10 kilovolts by an LC network having the 150 volt square wave voltage input to it. In particular, the power driver 130 is connected to a capacitor 140 which is in series resonant arrangement with the primary winding 150 of a transformer having a primary winding 150 and a secondary winding 170. The high-Q properties of the resonant circuit permit the higher-voltage (5-10 kV) sinusoidal signal to be formed at node 145. The primary winding 150 is grounded to power supply ground at 154.

The primary winding 150 is electrically connected to the secondary winding 170 at node 145, and is also magnetically coupled to it by a ferrite core 160. The primary and secondary windings are wrapped around the ferrite core 160. The ferrite core increases the Q of the LC circuit as seen by power driver 130. The transformer has a 10:1 turns ratio so as to step up the primary voltage so that the secondary winding provides a high voltage (about 100 kV) output signal.

The secondary winding is "air grounded" at 174 through a discharge pin 320. The secondary winding produces the voltage in the 30 kilovolt to 200 kilovolt range, resulting in the desired corona discharge beam. Charge gathers at the end of the discharge pin, which is preferably configured as a conductive (preferably bronze) rod.

Figure 6:
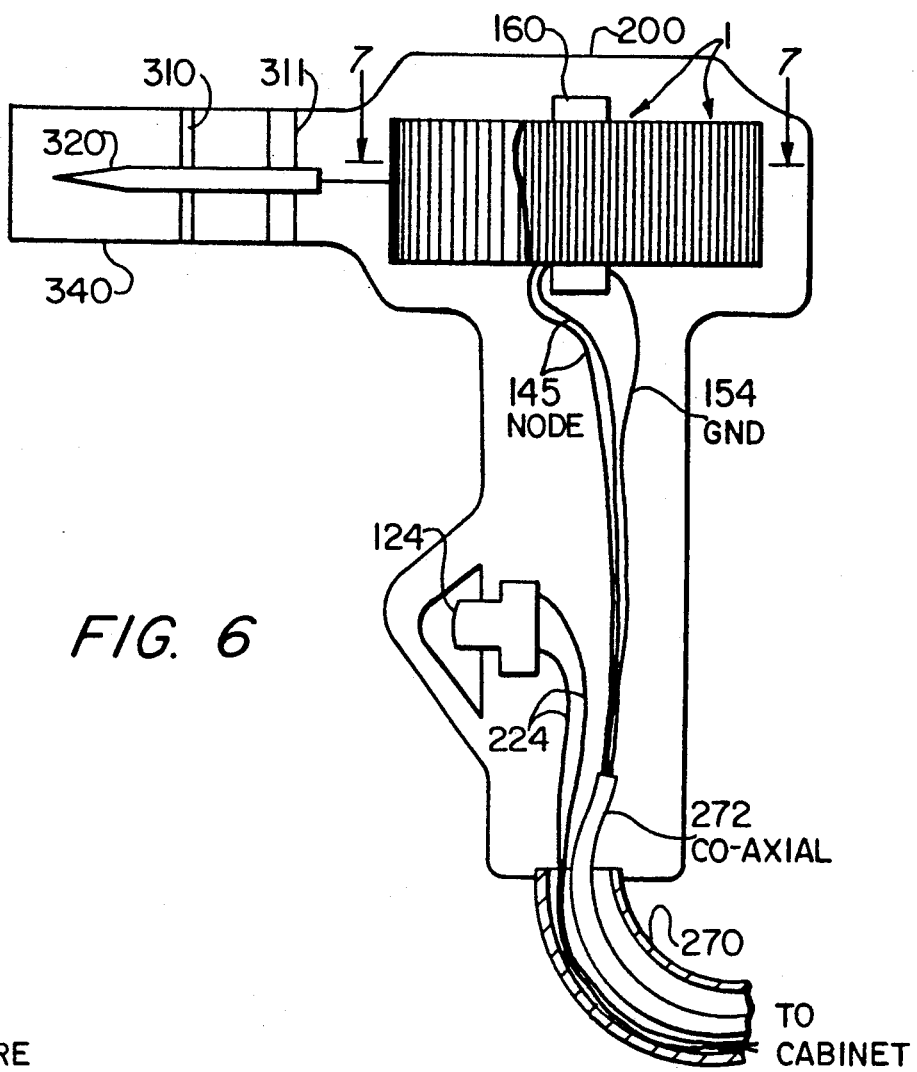
FIG. 6 is a side view, partially cut away, showing a preferred embodiment of the corona discharge apparatus according to a preferred embodiment of the present invention.

As shown in FIG. 6, an exemplary illustrated coil assembly 1 and associated discharge pin 320, resonant circuit node leads 145, the connection to power supply ground 154, and the trigger switch 124 are illustrated within a housing 200. Also illustrated are insulative support structures 310, 311 in the barrel 340 of the apparatus. The leads in node 145 to the primary and secondary coils, the return ground 154 wire, and the leads 224 from momentary switch 124, are all passed within a protective sheathing 270. The leads in node 145 to the primary and secondary coils, and the return ground 154 wire are respectively connected to the inner conductor and outer conductor of a co-axial cable 272 within the protective sheathing 270.

The opposite end of the protective sheathing 270 is connected to a cabinet (not shown) that includes other elements of the embodiment shown in FIG. 1. In the illustrated embodiment, elements 100-140 are in the cabinet, with only the coil assembly 1 and discharge pin 320 being in the hand-held corona discharge unit. However, it is contemplated that the capacitor 140 may be included not in the cabinet, but rather in the hand-held unit.

Figure 8:
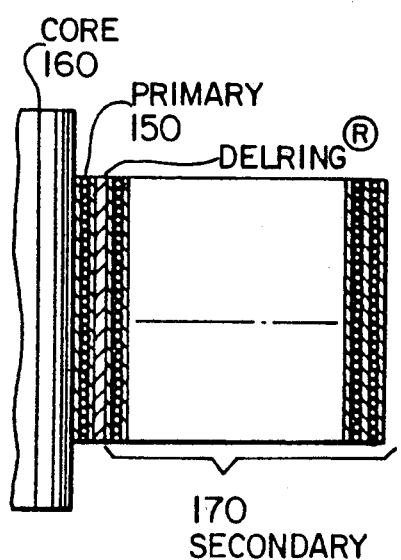
FIG. 8 is a side sectional view of the coil assembly according to a preferred embodiment of the present invention.
Figure 7:
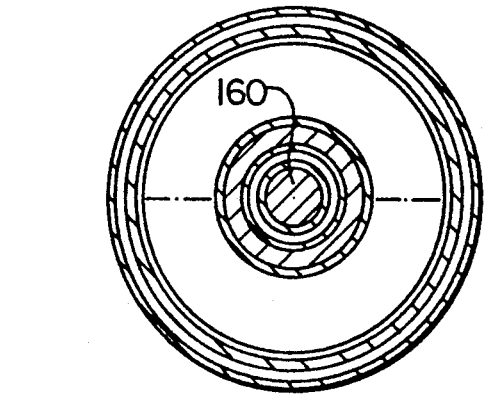
FIG. 7 is a top sectional view showing a preferred embodiment of the coil assembly, along line 7—7 of FIG. 6.

FIG. 7 is a top view showing a preferred embodiment of the coil assembly, along line 7—7 of FIG. 6. FIG. 8 is a side sectional view of the coil assembly according to the embodiment of FIG. 6.

As shown, the coil assembly is arranged in a substantially radial fashion, with the substantially cylindrical ferrite core 160 at its center. The ferrite core 160 is at ground potential. In the coil assembly generally, voltage increases with increasing distance from the center, with the highest voltage at the outermost portion of the assembly.

Progressing from the center, the coil assembly is constructed in layers, as seen most easily in FIG. 8.

1. The ferrite core 160. In the preferred embodiment, its diameter is 0.93 inches; its length is 3.1 inches; its preferred composition is MN80, available from MAGNETIC CERAMICS.
2. A layer of high voltage insulating tape capable of insulating voltage in excess of 10 kV. 0.003×1.5 inches.
3. The primary winding 150, which is 40 turns of Litz 8/30 wire. In this embodiment, only one layer of wire is necessary.
4. Another layer of high voltage insulating tape.
5. A slipover tube; preferably of DELRIN ®, inside diameter 1.042 inches, thickness of 0.135 inch, and length of 2.5 inches.
6. Another layer of high voltage insulating tape.
7. The secondary winding 170, comprising 400 turns of Litz 8/30 wire. The 400 turns are arranged in 20 layers, 20 turns per layer, each layer being separated from the next by respective layers of high voltage insulating tape. Approximate outside diameter, 3.1 inches. The wire itself is solid, with the conductor 0.016 inches in diameter with the total wire diameter, including insulation, being 0.038 inches.
8. A final layer of high voltage insulating tape.

The leads of input node 145 to the two windings, as well as the power supply ground lead 154 to the shield, are connected to the windings in respective layers closest to the ferrite. In contrast, the output 172 from the secondary, leading to the discharge pin 320, is taken off the outermost periphery of the secondary winding.

Figure 9:
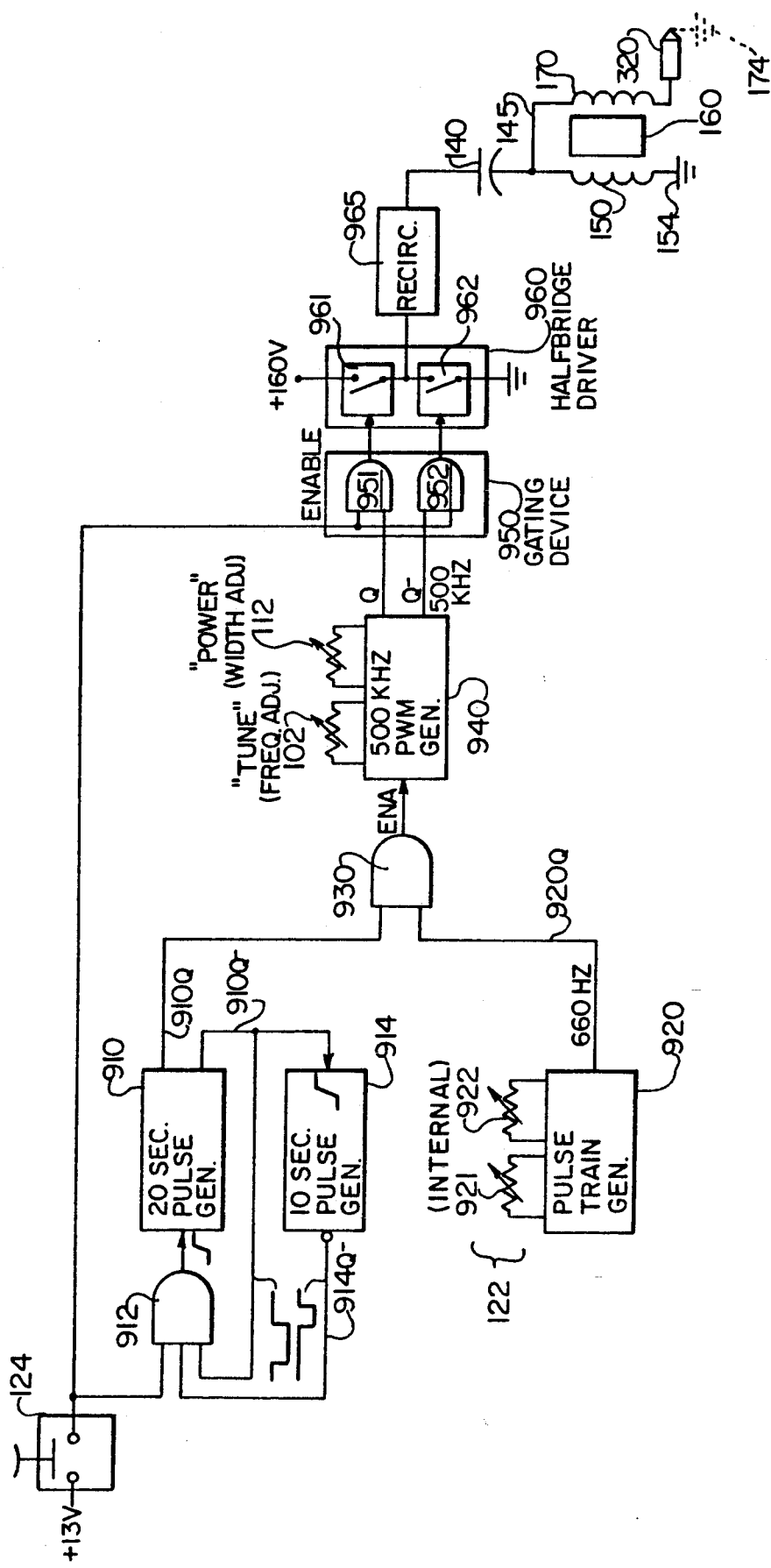
FIG. 9 is a block diagram schematically illustrating structure of a preferred embodiment of the corona discharge apparatus.

FIG. 9 is a block diagram schematically illustrating a preferred embodiment of the corona discharge apparatus. FIGS. 10A, 10B, and 10C (collectively referred to as FIG. 10 herein, for brevity) comprise a detailed circuit level diagram of the embodiment shown functionally in FIG. 1 and schematically in FIG. 9. FIG. 9 thus provides a closer representation of the structure shown in the detailed circuit diagram in FIG. 10, than does the very general functional diagram in FIG. 1.

Referring now to FIG. 9, switch 124 is shown as a momentary switch which shorts a positive constant voltage to a first input of an AND gate 912. AND gate 912 provides a gated switch signal to a 20-second ON-time pulse generator 910. The ON-time pulse generator 910 effectively functions as a monostable multivibrator, providing non-inverting and inverting outputs 910Q and 910Q—, respectively.

As will be better appreciated from the discussion below, pulse generator 910 is called an ON-time pulse generator because, during the 20-second "window" defined by its output pulse, the output coil of the apparatus may be on. At times when the 20-second pulse is inactive, the coil cannot be on.

The inverted 20-second output pulse is fed back to a second input of the AND gate 912, to schematically illustrate that the ON-time pulse generator does not operate as a re-triggerable pulse generator. That is, after a first rising edge is encountered at the input of the pulse generator, signal 910Q— blocks any further rising edges that are caused by any repeated depressions of switch 124, from causing the pulse generator from beginning a new 20-second pulse.

The rising edge of inverted output signal 910Q— triggers a second pulse generator 914, which operates as a monostable multivibrator. Pulse generator 914 outputs a 10-second inverted pulse 914Q— to a third input of AND gate 912. This 10-second pulse thus extends by 10 seconds the input gating function provided by the 20-second pulse 910Q—. It is understood that FIG. 9 is schematic, and not literal, in nature; accordingly, it is assumed for this discussion that monostable multivibrator 914 has zero delay time, so that the two blocking pulses on respective paths 910Q− and 914Q− are deemed contiguous to form a continuous 30-second blocking function, and do not allow a "gap" between the two blocking signals to re-trigger pulse generator 910.

In this manner, after switch 124 is depressed, a single 20-second period defined by a pulse at output 910Q, followed by a 10-second period defined by a pulse at output 914Q−, ensure that no further pulse can be generated. Accordingly, single or repeated depressions of switch 124 during a thirty second period result in a 20-second 910Q pulse followed by at least a 10-second absence of a 910Q pulse. After this 30-second period, new or continued depression of the switch 124 may cause another 20-second-pulse/10-second-absence.

The signal on path 910Q is provided to a first input of an AND gate 930. A second input of AND gate 930 receives a repetitive gating signal on path 920Q generated from a pulse train generator 920.

Pulse train generator 920 provides a repetitive series pulses of time duration $t_{on}$ with intermediate off periods of duration $t_{off}$ therebetween. In a preferred embodiment, $t_{on}=t_{off}$ to provide a square wave, with $t_{on}+t_{off}$ representing a pulse train period of 1515.1 μs, corresponding to a pulse repetition frequency period of 660 Hz. Respective $t_{on}$ and $t_{off}$ adjustment means 921 and 922, such as adjustable resistors, are illustrated. Adjustment means 921 and 922 collectively correspond to duty cycle adjustment means 122 (FIG. 1).

In this manner, AND gate 930 gates the 660 Hz pulse train on path 920Q against the 20-second pulse on path 910Q. During the 20-second pulse, the output of AND gate 930 is essentially the same as the signal on path 920Q, having a duty cycle determined by the settings of adjustment means 921, 922 (122 in FIG. 1). For example, when $t_{on}=t_{off}$ (corresponding to a square wave output from pulse train generator 920), the output of AND gate 930 is also a square wave for the duration of the 20-second period.

AND gate 930 enables a frequency-tunable pulse width modulator (also referred to as a PWM generator) 940. When active, PWM generator 940 generates a digital pulse train such as that shown in FIG. 3, having a frequency determined by frequency tuning means 102, and of pulse width determined by width adjustment means 112.

In the preferred embodiment, the pulse frequency is about 500 kHz, finely tunable to match the resonant frequency of the LC circuit including capacitor 140 and primary winding 150. The pulse width is adjusted by the user as needed to provide more output power.

When the PWM generator is enabled, opposite-polarity pulse trains are provided on respective paths 940Q and 940Q−. Each of these signals is represented by a waveform such as that shown in FIG. 3, gated by a 660 Hz signal so that it is represented by FIG. 4. Thus, it is understood that the signal in FIG. 3 is output by the PWM generator only when the pulse train on path 920Q is high; if the signal on path 920Q is between pulses, AND gate 930 disables the PWM generator so that its output goes to zero as shown in FIG. 4.

Based on the foregoing discussion, when there is no 20-second pulse on path 910Q, the PWM generator is disabled. Only for the duration of any 20-second pulse on path 910Q does the PWM generator generate a 500 kHz signal, and then, only during the μs "on" time periods of the 660 Hz enabling pulse train on path 920Q.

The opposite-polarity pulse trains provided on respective paths 940Q and 940Q− are input to respective inputs of a dual gating device 950. Dual gating device 950 includes two gates 951 and 952 which receive the signals on paths 940Q and 940Q−, respectively. Both gates 951, 952 of dual gating device 950 are enabled by closure of momentary switch (user push button) 124. Thus, the gated, opposite-polarity 500 kHz pulse width modulated signals on paths 940Q and 940Q− pass through the gates 951, 952, only at instants when the user is depressing the momentary switch (trigger) 124. By removing his finger from the push button 124, the user may almost instantaneously remove power from the coils by disabling the outputs of gating device 950.

The opposite-polarity outputs of dual gating device 950 are input to half-bridge power switch arrangement 960. Half-bridge power switch arrangement 960 includes two series-connected power switches 961, 962 disposed between a higher voltage (such as 160 V) than the voltage (such as 13 VDC) used by the logic in elements 910–950. When enabled, power switches 961, 962 collectively cause generation of an exponentially increasing sine wave in the high-Q LC circuit 140/150. The exponentially increasing sine wave is generated in the high-Q circuit constituting capacitor 140 and primary coil 150, through a recirculating means schematically illustrated as element 965.

The sine wave builds exponentially to the 5 kV to 10 kV range at the input of the primary winding 150, the exact range being dependent on the Q of the LC circuit comprising capacitor 140 and primary winding 150. The voltage provided by the secondary winding 170 to the corona discharge pin 320 is determined by the turns ratio (such as 10-1) of the secondary winding to the primary winding. In the preferred embodiment, the voltage across the secondary, which corresponds to the voltage from the discharge pin 320 to "air ground" 174, is approximately 100 kV.

In summary of the operation of FIG. 9, several conditions must concur for power to be delivered to the discharge pin 320. The user must depress the push button (momentary switch) 124 at least momentarily, to generate a 20-second pulse on path 910Q so that AND gate 930 is "on" during the high periods of the pulse train on path 920Q. Also, the user must wait at least 30 seconds from a previous triggering of a 20-second pulse on path 910Q, before another pulse may be generated. (The extra 10-second waiting period included in the 30 seconds ensures the components do not overheat, considering the high voltages involved.) Moreover, the user must continue to depress the momentary switch 124, in order to allow gating arrangement 950 to pass the 500 kHz signal to the half bridge power driver arrangement 960 and thence to the coils.

In the preferred embodiment, adjustment means 102 and 112 are readily accessible to the user. The frequency adjustment means 102 is aptly labelled "TUNE" near a rheostat knob or the like. The pulse width adjustment means 112 is aptly labelled "POWER" near another rheostat knob or the like.

However, gating pulse train duty cycle adjustment means 921, 922 (122) are preferably located inside a cabinet of the apparatus, so that they are not readily accessible to the user. Gating pulse train adjustment means 921, 922 (122) are set at the time of manufacture or for maintenance purposes by individuals who are generally more skilled than end users. Gating pulse train adjustment means 921, 922 (122) effectively determine a settable maximum power available to the device, with POWER knob 112 controlled by the user to adjust instantaneous output power from zero to that maximum. In this manner, gating pulse train adjustment means 921, 922 (122) ensure that, even at the maximum POWER setting on element 112, no elements will be burned out by the user.

The elements in FIG. 9 may be located in a variety of ways. The electronics shown as elements 910 through 965 are located in a suitable cabinet (now shown) separate from the hand-held unit shown in FIG. 6. The capacitor 140 may be located either in the cabinet, or in the handle of the hand-held unit, as desired. A suitable cable joining the cabinet to the hand-held unit must carry high voltages if the capacitor is located in the cabinet rather than in the hand-held unit. However, the hand-held unit can be made lighter and more compact by locating the capacitor in the cabinet.

FIGS. 10A-10C are a detailed circuit diagram of the embodiment shown more functionally in FIG. 9. Given the foregoing detailed description of FIG. 9, those skilled in the art will readily appreciate the function of the detailed disclosure in FIGS. 10A-10C. Thus, the following description is provided for convenience in facilitating an understanding of the non-limiting embodiment described herein.

Referring now to FIG. 10A, the push button (momentary switch) 124 is illustrated. A 2N2222 transistor is turned on by closure of the switch, and provides an inverting function to enable (active low enable) the dual gating arrangement 950 (FIG. 10C). The gating arrangement 950 is implemented as an INTERNATIONAL RECTIFIER IR 2110 driver/voltage translator.

In FIG. 10A, the first "555 timer" 910' has its pin 6 connected to an intermediate node of an RC timing network which governs the 20-second and 10-second timing pulses shown symbolically in FIG. 9. The 44 μF capacitor connected to ground is a timing capacitor, with the discharge path through the 100 kΩ resistor governing the 10-second blocking pulse shown symbolically on path 914Q− (FIG. 9).

Still referring to FIG. 10A, the second "555 timer" 920' is a free-running timer generating the 660 Hz, preferably square wave, pulse train on path 920Q (FIG. 9). Rheostats 921, 922 have exact analogs in FIG. 9.

Still referring to FIG. 10A, the AND gate 930 (FIG. 9) is embodied by a joining of the wire outputs of the two "555 timers" 910', 920'. This joining effectively performs a gating function at the input to pulse width generator 940' (FIG. 10B).

Referring to FIG. 10B, pulse width generator 940' is preferably implemented using an SG3525A or equivalent. TUNE and POWER rheostats 102, 112 (FIG. 9) find analogs 102', 112' in FIG. 10B. Also illustrated in FIG. 10B is circuitry devoted to converting 115 VAC power into 13 VDC power for use as a DC power supply for the digital circuitry. The invention provides that DC battery power may also be used to power the device, in which case the illustrated AC-DC conversion circuitry may be replaced by suitable DC power circuitry.

Referring to FIG. 10C, the dual gate arrangement 950' is shown, implemented as an IR2110. The dual gate arrangement 950' drives respective FETs (field effect transistors) 961', 962' within half bridge driver 960'. A central node between the FETs of half-bridge driver 960' drives the high-Q circuit 140/150 through an arrangement of four fast diodes collectively indicated as recirculation means 965'. The diodes are arranged in a FIG. "8" configuration, with the half-bridge's intermediate node and capacitor being connected to the extreme ends of the "8". Also, two fast diodes connect in series (1) ground potential, (2) the node between the recirculation means 965' and the capacitor 140, and (3) the +160 V node.

Respective diodes connect the source to the drain of each of the two FETs 961', 962', to by-pass the FETs on one direction.

In FIG. 10C, the 160 V level is generated by a conversion circuit receiving 115 VAC power, the details of which are not central to the present invention. The invention provides that DC battery power may also be used to power the device, in which case the illustrated AC-DC conversion circuitry may be replaced by suitable circuitry for producing the 160 V level.

As will be appreciated by those skilled in the art, various RF filter capacitors are provided between DC power and ground, physically close to various circuit elements, due to the high voltage and current changes generated within the apparatus.

During operation, the FET switches 961', 962' are turned on and off in opposite phase, controlled by the (approximately) 500 kHz square wave signals input to their respective gates. In this manner, because the (approximately) 500 kHz signal is tuned precisely to the resonant frequency of the LC circuit 140/150, the high-Q properties of the resonant circuit allow it to support a cumulatively increasing voltage as fed by the two FETs in successive half-cycles of the 500 kHz waveform.

The process by which the voltage in the resonant circuit cumulatively increases may be understood as follows.

First, assume FET 961' is turned on during a first half of a first cycle of the 500 kHz waveform, causing node 145 to achieve a first voltage of a first polarity. Then, during the second half of the first 500 kHz cycle, FET 962' causes the node to achieve a second voltage twice that of the first, but of opposite polarity. During the first half of a second cycle of the 500 kHz switching signal, the first FET 961' causes the node to achieve to a third voltage larger in magnitude than the second voltage, but in the first polarity. During the second half of the second cycle, the second FET 962' causes the node to achieve a fourth voltage greater in magnitude than the third voltage, in the second polarity.

This process continues, with the instantaneous AC peak voltage at the node increasing to a limit determined by the Q of the LC circuit and by the exactitude of the tuning of the frequency to the resonant frequency of the LC circuit. In this manner, if the frequency is exactly tuned to the resonant frequency of the LC circuit, the current and voltage experienced by the LC circuit builds rapidly to a maximum, displaying a waveform such as that illustrated schematically in FIG. 5.

Thereafter, if any of the following conditions occur, the process reverses:

1. The 20-second interval determined by pulse generator 910 (FIG. 9) terminates, causing AND gate 930 to disable PWM generator 940.
2. A pulse in the pulse train on path 920Q goes inactive, so that AND gate 930 disables PWM generator 940.

3. The user lifts his finger from the push button (momentary switch) 124, so that dual gate arrangement 950 is disabled.

In any of these circumstances, because either the PWM generator 940 or the gating arrangement 950 are disabled, the switching FETs in half-bridge driver 960 are switched off, so that additional power is no longer provided to the resonant LC circuit 140/150. In this event, the waveform shown in FIG. 5 decays to zero, in a time substantially determined by the Q of the LC circuit.

The invention also provides a self-tuning embodiment to ensure that the frequency of the PWM generator is maintained at the resonant frequency of the LC circuit 140, 150. The self-tuning feature ensures that no manual adjustment of frequency of the PWM generator 940 is necessary. This implies that the TUNE (frequency adjustment) knob 102 is not necessary.

Modifications of the manual tuning embodiment required to convert it to the self-tuning embodiment are shown in FIG. 11. In the self-tuning embodiment, a resistor $R_{s.t.}$ is inserted between the primary winding 150 and power supply ground 154. The resistor is effectively used to measure the current passing through the primary winding. The node between the resistor and the primary winding is used as a measurement output.

As shown in the manual tuning embodiment of FIG. 10B, a capacitor extends to ground from pins 5 and 7 of the SG3525A PWM generator. However, to convert the FIG. 10B embodiment to a self-tuning embodiment, the formerly grounded end of the capacitor is connected directly to the measurement output of the primary winding, as shown in FIG. 11.

Modifications and variations of the above-described embodiments of the present invention are possible, as appreciated by those skilled in the art in light of the above teachings. For example, the particular frequencies, signal magnitudes, power supply magnitudes, physical dimensions, electrical characteristics, chip implementations, and timing characteristics of components of the illustrated embodiments may be varied in accordance with principles known to those skilled in the art, without departing from the scope of the invention. It is therefore to be understood that, within the scope of the appended claims and their equivalents, the invention may be practiced otherwise than as specifically described.

What is claimed is:

1. An apparatus for producing a corona discharge, comprising:

means for producing a digital signal made up of low-frequency bursts of high-frequency width-modulated pulses;

means for transforming the signal into a high-voltage signal power magnitude varies directly with the pulse widths; and means for producing the corona discharge in response to the high-voltage signal.

2. An apparatus for producing a corona discharge, comprising:

means for generating a first frequency signal;

means for pulse-width modulating the first frequency signal to produce a pulse-width modulated signal;

means for periodically gating the pulse-width modulated signal at a second frequency slower than the first frequency, so as to produce a gated signal including bursts of width-modulated pulses at the first frequency;

resonant means for transforming the gated signal into a high-voltage signal having a power proportional to the modulated pulse widths and to the gating; and means for producing the corona discharge in response to the high-voltage signal.

3. An apparatus for producing a corona discharge, comprising:

a) a pulse width modulation (PWM) generator for generating a PWM output signal, the PWM generator including:

1) means for adjusting a frequency of the PWM output signal, positioned to be readily accessible to a user of the apparatus; and 2) means for adjusting width of pulses in the PWM output signal, positioned to be readily accessible to the user;

b) a momentary switch positioned to be readily accessible to the user;

c) timer means, responsive to the momentary switch, for producing a window signal for only a given period immediately after a depression of the momentary switch;

d) a gating pulse train generator means for generating a pulse train of a frequency substantially lower than the frequency of the PWM output signal, the pulse train having periodic enabling periods;

e) AND gate means for receiving (1) the window signal from the timer means and (2) the pulse train from the gating pulse train generator means, and for enabling the PWM generator only during the concurrence of the window signal and the enabling periods;

f) means for gating the PWM output signal whenever the momentary switch is not depressed;

g) driver means, responsive to the gating means, for producing a driving signal indicative of the PWM output signal when the gating means does not gate the PWM output signal;

h) a capacitor, disposed between the driver means and a coil assembly;

i) the coil assembly, responsive to the driver means, the coil assembly including:

1) a primary winding which, with the capacitor, forms a resonant circuit at the frequency of the PWM generator, the resonant circuit causing substantial magnification of the voltage of the driving signal;

2) a substantially cylindrical core, disposed physically about a central axis about which the primary winding is located;

3) a secondary winding, wound around the central axis at a radius therefrom greater than that of the primary winding, the secondary winding being magnetically coupled to the primary winding by the core and having a greater number of turns than the primary winding so as to provide a high voltage transformer output; and j) a discharge structure which is connected to the secondary winding to receive the high voltage transformer output, so as to generate the corona discharge in a manner substantially governed by the driving signal and PWM output signal.

4. A method of producing a corona discharge, comprising:

generating a digital signal made up of low-frequency bursts of high-frequency width-modulated pulses;

transforming the signal into a high-voltage signal whose magnitude is proportional to the width of the pulses; and producing the corona discharge in response to the high-voltage signal, the characteristics of the corona discharge being determined in part by the bursts of the high-frequency width-modulated pulses.

5. A method of producing a corona discharge, comprising:

receiving a trigger signal indicative of closure of a momentary switch operated by a user;

producing a window signal in response to the trigger signal;

producing a periodic gating signal of period substantially less than the duration of the window signal;

producing a PWM enabling signal at the concurrence of the window signal and an enabling level of the periodic gating signal;

generating a PWM output signal upon the occurrence of the PWM enabling signal, the PWM output signal constituting a series of bursts of pulses of frequency substantially higher than that of the periodic gating signal and of width determined by a pulse width adjustment means accessible to the user;

gating the PWM output signal instantaneously whenever the trigger signal is not present;

producing a driver signal whenever the PWM signal is generated and not gated;

converting the driver signal to an intermediate voltage signal greater in magnitude than the PWM signal, using a series resonant circuit having a resonant frequency substantially equal to the PWM output signal's frequency, the series resonant circuit including a capacitor and a primary winding of a transformer;

stepping up the intermediate voltage across the primary winding to a high voltage across a secondary winding of the transformer; and feeding the high voltage to a discharge structure so as to produce the corona discharge.

6. A coil assembly, comprising:

a substantially cylindrical ferrite core, concentrically arranged with an imaginary axis of the coil assembly;

an input lead means for receiving an intermediate magnitude AC voltage signal;

a primary winding constituting a conductive wire wrapped about the ferrite core, the primary winding connected to the input lead means and to ground;

a hollow cylindrical separation structure, disposed closely about the primary winding;

a secondary winding, also connected to the input lead means, and constituting a conductive wire wrapped about the hollow cylindrical separation structure, the secondary winding including a plurality of layers greater than that of the primary winding so as to embody a turns ratio substantially greater than one;

an output lead means extending from the secondary winding to a discharge structure for providing to the discharge structure a high voltage signal of a magnitude sufficient to produce a corona discharge; and a plurality of layers of insulating material disposed between layers and elements which would otherwise conduct electricity between layers;

wherein the foregoing elements are arranged radially away from the imaginary axis of the coil assembly in the order recited above.

* * * * *